(12) United States Patent
De Vandiere et al.

(10) Patent No.: US 7,411,671 B2
(45) Date of Patent: Aug. 12, 2008

(54) TECHNIQUE FOR ANALYZING BIOLOGICAL COMPOUNDS IN A NON-DESTRUCTIVE MODE

(75) Inventors: Bruno De Vandiere, Clermont Ferrand (FR); Claude Debroche, Cebazat (FR); Francis Galibert, Saint Gratien (FR)

(73) Assignee: Flowgene SA, Saint Bauzire (FR)

( * ) Notice: Subject to any disclaimer, the term of this patent is extended or adjusted under 35 U.S.C. 154(b) by 0 days.

(21) Appl. No.: 11/522,502

(22) Filed: Sep. 15, 2006

(65) Prior Publication Data

US 2007/0103680 A1    May 10, 2007

(30) Foreign Application Priority Data

Sep. 15, 2005   (FR)   ................... 05 09667

(51) Int. Cl.
*G01J 3/44* (2006.01)
*G01N 21/65* (2006.01)
(52) U.S. Cl. .................................................. 356/301
(58) Field of Classification Search ................. 356/301
See application file for complete search history.

(56) References Cited

U.S. PATENT DOCUMENTS

| 4,832,483 | A | 5/1989 | Verma |
| 4,847,198 | A | 7/1989 | Nelson et al. |
| 5,814,516 | A | 9/1998 | Vo-Dinh et al. |
| 6,040,906 | A | 3/2000 | Harhay |
| 6,844,199 | B1 | 1/2005 | Nelson et al. |
| 2003/0073139 | A1 | 4/2003 | Kreimer et al. |
| 2003/0194798 | A1* | 10/2003 | Surber et al. ............. 435/252.1 |
| 2004/0039269 | A1 | 2/2004 | Ward et al. |

FOREIGN PATENT DOCUMENTS

| WO | WO 98/41842 | 9/1998 |
| WO | WO 03/060444 A | 7/2003 |
| WO | WO 2004/048937 A | 6/2004 |
| WO | WO 2005/059523 A | 6/2005 |

OTHER PUBLICATIONS

M.C. Storrie-Lombardi, "Hollow cathode ion lasers for deep ultraviolet Raman Spectroscopy and Fluorescence imaging", Review of Scientific Instruments, vol. 72, No. 12, Dec. 2001, pp. 4452-4459.

* cited by examiner

*Primary Examiner*—F. L Evans
(74) *Attorney, Agent, or Firm*—Cohen Pontani Lieberman & Pavane LLP

(57) ABSTRACT

A medium is analyzed for the search for an odorous biological molecule characteristic of a specific substance in an environment to be studied comprising the steps of: exposing a component containing at least one olfactory biological receptor, capable of selectively attaching the type of odorous molecule sought, to an atmosphere taken from the environment to be studied; irradiating that component by means of an incident laser radiation having a wavelength chosen in the ultraviolet close to the absorption wavelength for the olfactory receptor, to cause the excitation of a resonance Raman scattering in the irradiated component; and analyzing the Raman spectrum obtained to determine whether or not it corresponds to the Raman spectrum of the olfactory receptor having attached an odorous molecule of the type sought in the atmosphere sampled, so as to identify any presence of the specific substance mentioned in the environment to be studied.

23 Claims, 4 Drawing Sheets

TECHNIQUE FOR ANALYZING BIOLOGICAL COMPOUNDS IN A NON-DESTRUCTIVE MODE

TECHNICAL FIELD

This invention relates to an optical method and device for studying and analysing chemical compounds and in particular biological compounds in a non-destructive mode. In particular, it may be applied for real-time monitoring of changes in the structure of an excited component as a function of its environment.

PRIOR ART

Certain continuous analysis methods for physico-chemical phenomena call on techniques based on sensors. A physico-chemical phenomenon may be a change in temperature, pressure, pH or concentration, etc. The element which provides the means for translating such a physico-chemical phenomenon and its variations into data which can be used electrically (or electronically) is usually referred to as a sensor.

Biology is one of the scientific sectors which make great demand for measurement and detection technologies. Indeed it is often difficult to convert data of a biological origin into usable data which may take the form of an electric signal.

In response to this problem, scientists are seeking to get as close as possible to the behaviour of biological phenomena. This is the case, for example, for odour detection. Work by Richard Axel and Linda Luck (1991) highlighted the existence of olfactory receptors in mammal sensory organs. To date, the instruments which have been developed to provide the detection of odours use technologies based on sensors which come mainly from the micro-electronics world. They are neither sensitive nor selective enough and have performance which is a long way from that of a natural nose (human or animal).

It was thus very tempting to study the operation of olfactory neurons and to try to extract from them the specific receptors which could potentially be used to detect a smell or, more specifically, odorous molecules. Accordingly, much work was carried out to identify this operating principle and one of the most interesting proposals is based on the use of recombinant protein(s) resulting from the gene sequence coding the olfactory receptors. If the sequence is chosen correctly, this recombinant protein (or these recombinant proteins) is (are) liable to bind itself (or themselves?) specifically to the relevant odorous molecule or molecules.

Olfactory receptors (OR) are part of the protein receptors class, i.e. proteins on which small molecules, called ligands, can attach themselves in a specific way. In living cells there are several types of receptors which among other things are characterised by their location. For example, one talks of nuclear or cytoplasmic receptors. Ligand-receptor recognition is highly specific. Like a key which fits into and operates a lock, a ligand attaches itself to its receptor by pattern recognition. The ligand's attachment to its receptor results in a cascade of biological reactions which end up with a specific biological effect.

Thus the olfactory receptors attach the volatile odorous molecules in a specific way. In mammals, there is a very large set of olfactory receptors (several hundred) which provide recognition of tens of thousands of chemically-different odours. The olfactory receptors are fixed in the olfactory neuron cytoplasmic membrane, the olfactory neurons themselves being located on the surface of the olfactory mucous membrane. The attachment of an odour onto its receptor triggers a series of reactions which end up in the transmission of a signal, via the olfactory bulb, to various areas of the brain where they are processed (recognised, memorised, etc.). The olfactory receptors belong to the broad family of GPCR (Guanine Protein Coupled Receptor), receptors for which the transmission of the signal activates a "G binding protein".

Research intended to identify smells automatically were thus directed to the use of the change in structure which affects the olfactory receptors as a consequence of the attachment by them of their specific odorous molecules.

At this stage, this research came across the difficulty of knowing which physical measurement to be used to identify the difference between an olfactory receptor on its own and that receptor when it is bound to an odorous molecule, or more generally, a protein receptor, depending on whether or not it is attached to its or one of its specific ligands.

There are various techniques available in analytical chemistry for analysing a molecule's structure.

The most common is mass spectrometry. This technique provides the means for identifying very exactly the atoms which go into the molecule's composition. It provides extremely precise information on the various components of a molecule. Nevertheless, Mass spectrometry has two substantial disadvantages. Firstly, it is a destructive technique. The sample is permanently destroyed during the analysis. It is thus not possible to study the changes in a molecule in a continuous process. Secondly, it is a technique which provides the means for identifying the composition of a molecule, but not its change in conformation. Indeed, a molecule's composition remains unchanged when it changes shape. Mass spectrometry is thus not suitable for resolving the problem.

Another method is based on fluorescence. A fluorescent marker is grafted onto an olfactory or other receptor. In principle, this fluorescence should be altered by the attachment of the odorous molecule or other ligand. This technology has two main weaknesses: grafting the marker inevitably disrupts the receptor's operation and the variation in fluorescence following a molecule's attachment is itself very slight.

Another technique on which much work has been carried out since its discovery in 1928 is based on the Raman effect (Chandrasekhara Venkata Raman, Nature, 121-619, 1928).

When a laser excites a component at a given wavelength, different light-matter interactions may then occur. The main ones are:

Rayleigh scattering: elastic scattering of the incident beam with no loss of energy, the scattered radiation can be observed at the same wavelength as the incident beam.

fluorescence: the incident radiation is absorbed and causes a change in state of one of the component's electrons which thus finds itself in an excited state; as the system is returned to its initial state it emits light at a greater wavelength than that of the incident beam (This process induces a high energy loss).

Raman scattering: inelastic scattering of the incident beam with a slight energy loss linked to a certain vibration mode (structural vibrations) of the component. The light scattered in this way can be observed in the spectrum close to the incident light (very low energy loss).

As the output from this latter process is very low, the intensity of the scattered beam is approximately ten million times weaker than that of the incident light.

Much work has attempted to get the most out of the potential offered by the Raman Effect. For example, the Raman Effect may be used to identify diseases by analysing the Raman Effect coming from blood plasma (Verma, Method of using resonance Raman Spectroscopy for Detection of Malignancy Disease, U.S. Pat. No. 4,832,483; May 23, 1989,). Scientists have also used it to identify bacteria in suspension in a liquid (Nelson et al., Detection and Identification of Bacteria by means of Ultra-violet Excited Resonance Raman Spectra, U.S. Pat. No. 4,847,198, Jul. 11, 1989). The use of the Raman effect has also been proposed for identifying molecules or biomolecules (Harhay, Resonance Raman Spectroscopy for Identifying and Quantitating Biomatter, Organic, and Inorganic Analytes, U.S. Pat. No. 6,040, 906, Mar. 21, 2000).

More recently, work has shown that it is possible to use the Raman effect to study biochemical component bindings. Thus, the study of bacteria binding with antibodies by Raman spectroscopy was described by Nelson and at. (Direct Detection of Bacteria-Antibody Complexes via UV Resonance Spectroscopy, U.S. Pat. No. 6,844,199 B1, Jan. 18, 2005).

Nevertheless, the study of compounds by Raman Effect remains difficult: a Raman spectrum is complex and appears as a sequence of peaks. One problem is identifying and understanding the significance of these peaks which quickly becomes difficult for biological elements. Moreover, the reliability of the information given by a Raman spectrum quickly becomes questionable and thus unusable. To illustrate this problem, work carried out by Kreimer on the binding of compounds on a surface (Surface Enhanced Raman Spectroscopy, SERS) has shown that it was possible to overcome this reliability problem by analysing simultaneously this type of Raman spectrum with a surface plasmon resonance spectrum (Surface Plasmon Resonance, SPR)—see Kreimer and al., Devices and Methods for verifying Measurement of Analytes by Raman Spectroscopy and Surface Plasmon Resonance, US Patent 2003/0073139A1, Apr. 17, 2003.

Without doubt because of the difficulties stated above, a means of detecting the presence of certain odours automatically, without calling on living beings, is thus still being sought, in particular where those odours may be sought as characteristic of the presence of certain substances in an environment to be studied and more specifically again, in this case, where the odour molecules may only be present as traces in the ambient atmosphere.

STATEMENT OF INVENTION

An object of this invention is to resolve this problem and the difficulties stated above to detect a change in the properties, in particular a conformation change in a biological receptor under the effect of a ligand. It covers specifically the detection of such changes in olfactory biological receptors (OR) under the effect of odorous molecules.

The invention is based on the use of the Raman effect properties when the biological receptor is excited with a laser beam.

It comprises, in particular, a process or method for detecting in a medium to be investigated the presence of a ligand capable of combining with a biological receptor, including the steps of: exposing a sample of the medium to be investigated to a component containing the biological receptor in question; irradiating said component with incident laser radiation whose wavelength is chosen in the ultraviolet close to the biological receptor's absorption wavelength to produce a resonance Raman scattering effect in the component irradiated; and analysing the Raman spectrum obtained to determine whether or not it corresponds to the Raman spectrum for the receptor having attached a ligand of the type sought. The biological receptor used in the sensor may be in its natural state or obtained by genetic engineering.

Raman resonance scattering is understood to mean the Raman effect obtained when the component to be studied is excited with a wavelength located in the vicinity of the component's absorption spectral zone in the ultraviolet. The yield of the Raman process in this spectral zone is amplified and the intensity of the scattered beam much greater than for traditional Raman scattering.

Because of its physical nature, the Raman effect depends not only on the composition but also on the structure or better here on the conformation of the molecule of the receptor in question. According to one aspect, the invention is based on the fact that the light spectrum resulting from resonance Raman scattering in the ultraviolet has characteristics which, thanks to its intensity and its position in the spectral wavelength scale, make it particularly suitable for revealing changes in structure of a protein receptor when its specific ligand or one of its specific ligands is present. One main advantage of this technique is that not only does it not affect the integrity of the receptor, but it may be carried out continuously.

Traditionally, two factors limit attempts at analysing molecular structures: firstly, sensitivity may turn out to be insufficient because the Raman effect produced involves a very low level of light energy; secondly, the identification of the exact spot in the Raman spectrum where it would be possible to detect a change in signal, to correlate it with the presence or otherwise of a molecule on the biological receptor, may prove to be a difficult operation.

There was a significant advance in 2001, with the outcome of UV lasers with relatively affordable terms on the financial front. This made it possible to show that the use of lasers operating in the UV (224 nm or 248 nm) substantially increased the level of the Raman effect emission compared with lasers operating in the visible wavelengths (between 400 and 800 nm) (Storrie-Lombardi M. C., Hollow cathode ion lasers for deep ultraviolet Raman Spectroscopy and Fluorescence imaging. American Institute of Physics. 2001).

In actual fact, the smaller the excitation wavelength, the greater the energy transmitted to the molecule, and thus the higher is the Raman energy emitted by the molecule. It may thus be of interest to use low wavelengths where possible. In this respect, the results of the Storrie-Lombardi publication showed that it is possible to use resonance Raman scattering to study the structure of a molecule. Moreover, the instantaneous power of these lasers, which is around 10 mW actual, is compatible with the molecules used in molecular biology, which is not true for so-called pulse lasers, where the instantaneous power may reach several kW and thus destroy the molecule irradiated.

Using these observations, certain research groups were able to identify bacteria, in particular combined with other components, by analysing resonance Raman scattering spectra in the UV, as evidenced by the references referred to at the beginning of this document. However, the low signal level available and even more the great complexity of the spectra obtained with this detection method prevent an analysis of complex compounds or those in multiple configurations as are frequently encountered in the field of living beings.

Thus it is that on continuing their studies on the detection of the association between the biological receptor and the ligand or ligands it is liable to bind to, in particular in the field of odour detection, the inventors tried to make use of another observation relating to the Raman scattering phenomena. It is known that the study of the Raman effect on a molecule can no longer be pursued beyond the excitation wavelength which relates to the appearance of "native" fluorescence, i.e. that which appears spontaneously in the matter in the absence of any marker. Indeed, the fluorescence signal is much greater than the Raman signal. The range of use for a Raman study is thus between the excitation wavelength and the start of fluorescence. It has been observed that, for a laser operating at 488 nm, a molecule's fluorescence starts at around 500 nm which means that the possible range of use for the Raman effect is between 488 nm and (at best) 500 nm, i.e. 12 nm. On the other hand, if we take the case of a laser operating at 224 nm, a molecule fluorescence starts at 290 nm. The range of use for a Raman study is then 66 nm! The greater is the range of use, the higher is the probability of detecting in the Raman spectrum changes which are representative of the change in structure linked to the association of a given biological receptor with one of its ligands.

Using that observation to identify a usable difference between a biological receptor alone and a biological receptor bound with a ligand, one can use the resonance Raman scattering effect produced by its excitation by a UV laser in a frequency band of between 200 nm and 300 nm approximately and to advantage between 200 nm and 250 nm approximately or even less in the lower part of the wavelengths where the output of the Raman spectrum emission is better, the 224 nm wavelength being preferred.

Unfortunately this arrangement does not always provide the means for overcoming a second practical difficulty, namely that UV lasers remain difficult to manipulate. Even so, the Raman signals recovered are of low amplitude and the experiments remained at research level. This is in particular the situation for the search for odorous molecules in a given medium for which one could have liked to bring the samples in contact with olfactory biological receptors for recognition purposes.

In this respect, according to another aspect, a technique of specific reflection may be used to collect effectively the radiation coming from a biological receptor when it is excited by a laser. This system has the significant advantage of being independent of the wavelength used, as opposed to conventional optical devices which use transparent components such as silica (lens, prism, etc.) for which the performance is directly linked to the wavelength being used.

Accordingly, it is proposed to use an optical device such as described in the French patent application FR 03 14519 and the International patent application No. WO 2005/059523 A1 to collect the Raman effect emitted by the biological receptors. This device not only provides excellent efficiency in collecting the Raman effect, but it is also compatible with the laser wavelength 224 nm which is the most effective and retains that property through the whole of the breadth of the spectrum in question.

Thus according to this aspect, this invention provides a non-destructive process or method of spectrum analysis of a sample of matter, wherein a quasi dotlike zone of such sample is irradiated with incident luminous radiation and all or part of the emergent radiation from the sample in response is detected, in another area which is spatially separate from the irradiated zone, to recover the spectrum reflecting the properties of the resonance Raman scattering for the sample under the effect of the incident radiation. In accordance with this method, the emerging radiation is recovered in a solid angle covering at least 10% of the whole of the beam scattered by Raman effect from the sample in a range of wavelengths close to the wavelength of the incident radiation to analyse a substantial part of the total light scattered by the sample excited.

Thus, for identifying a usable difference between a biological receptor on its own and a biological receptor to which a ligand is bound, the invention provides for using a non-destructive detection process, namely Raman scattering, combined with lasers operating in UV (224 nm for example) and a cell for collecting the light emitted, compatible with UV lasers and which can uniquely provide sufficient collection effectiveness to furnish a usable signal.

A key application of this method is the search for links between one or more olfactory biological receptors (OR) and odour molecules which may combine with those in respect of Ligands to provide the detection of odours with no animal or human involvement.

The application of the method is particularly critical when one is faced with a situation where the odour matter is in very low concentrations only, for example in the atmosphere surrounding objects or products liable to contain one or more substances sought, which have an odour, while not being able to work directly on the object or product in question, nor its packaging.

The interest of this sort of process can be understood in control or monitoring applications, for example on objects in transit or in the environment of installations to be monitored, applications for which until now only animals, in particular specially trained dogs, were able to be used with a degree of effectiveness which is sometimes good but eminently variable depending on the time and the individuals.

In this respect, not only is the method according to the invention non-destructive as regards olfactory biological receptors which are natural or obtained by genetic engineering and which may be relatively fragile, but it can also be applied to continuous measurement.

Indeed it is possible to record a complete Raman scattering spectrum on a sample containing given olfactory biological receptors in laboratory conditions and thus to identify any change made to that Raman scattering spectrum by a change in the olfactory receptors' environment. Thus by systematic study one can identify the spectral lines of the Raman spectrum which change in the presence of a specific odorous molecule.

The detection system can subsequently be locked onto one of those spectral lines which is specific for the odorous molecule of interest and analyse a gas, an atmosphere, etc. relative to that molecule continuously over time, and thus monitor the content of that molecule in the atmosphere being studied.

Thus for example one can take samples or a current of gas from the atmosphere surrounding the objects or products to be studied without opening any packaging they may have and let those samples or that current of gas pass over an olfactory receptor for which any changes in configuration are monitored. Thus one can work with a battery of olfactory receptors over which a current of gas to be analysed is passed and they are subjected sequentially to analysis according to the invention.

According to yet another aspect of the invention, a non-destructive spectrum analysis device for a sample of matter which is particularly suitable for the detection of odours in an environment to be studied comprises a means of presenting a quasi-dot like zone of the sample to incident luminous radiation and a means of collecting the luminous radiation coming from the sample in response to the incident radiation and to send it to a detection area. A particular feature of the device is that those particular collection means have a concave reflective surface arranged around an axis passing by the quasi-dot like zone which is capable of concentrating a substantial fraction of the light emerging onto that detection area and wherein the said reflective surface is made out of a material suitable for the reflection of ultraviolet rays in the 200 nm to 300 nm bracket, preferably between 200 nm and 250 nm and to advantage 224 nm. The concave reflective surface may be an elliptic mirror with a concave revolution, where the quasi-dot like zone and the detection area are placed respectively at two of the elliptic mirror focal points. The reflective surface may or may not be coated with a deposit, such as nickel, chromium, aluminium oxide, or magnesium fluoride. That deposit may have reflective and/or protective powers.

An embodiment of a device according to the invention includes means of presenting a sample intended to be irradiated by a laser beam and means of collecting the light given off by the sample in response. The presentation means comprises a fluid circulation device in the immediate vicinity of the samples quasi-selective zone, this containing at least one sensor liable to react in the presence of a ligand in the fluid. In an embodiment mode comprising a series of sensors placed side by side, a system of relative displacement between the sensors and the irradiation and collection device provides the means for analysing sequentially the state of the sensors (ligand presence or not) using a single excitation/detection means.

This device may consist of a support in the form of a narrow band made from a material which is transparent to UV (UV silica for example) and which is thin so as to limit interference due to variations in the refraction index, whether for the laser or for the light energy given off by the biological receptor. At the end of this support, the biological receptor is fixed onto the support by suitable means. This support may be used alone, in which case a fluid is brought onto the receptor by suitable means, or it may be inserted into a silica tube which is transparent to UV so that it is possible to make a fluid circulate inside that tube. The tube may have a circular, square, or rectangular section. The support, with or without tube, is installed in a hollow elliptical cell so that the biological receptor is placed in one of the two focal points and the tube axis, if a tube is used, is perpendicular to or at least close to the perpendicular direction relative to the ellipse axis of revolution. A laser beam may be conveyed to the biological receptor in an oblique direction relative to the ellipse's axis through an opening made close to the elliptical cell's second focal point. A second opening is provided in the extension of the laser beam to let the incident beam out of the elliptical cell, and a third opening around the laser beam reflection axis on the support also allows the laser beam rays reflected by the sensor and its support also outside the cell.

In an embodiment a spectrograph (or monochromator) is used to analyse the Raman scattering. It is positioned on the elliptical cell's major axis at its output. By virtue of its function, it selects a very narrow wavelength band from the light signal emitted. The narrower this band is, the more effective the spectrograph is. The light signal from this narrow band is collected by an optical sensor which may be a photo-multiplier tube, a CCD camera, a photon counter, or a detection diode. The type of sensor is selected according to the sensitivity required to collect the luminous signal. The spectrograph sweeps the narrow band along the whole of the spectrum, thus providing the means for analysing the whole spectrum point by point. In theory, the spectrograph should leave aside the frequency of the luminous energy relating to the excitation laser. In fact, that luminous energy coming from the various laser beam reflections considerably pollutes the operation of the spectrograph. To resolve this specific problem and to eliminate those luminous beams from the laser as far as possible, rejection optical filters could be used such as Notch-type filters available in visible light, i.e. above 400 nm. In the absence of a solution of this type in UV, an alternative approach currently has to be used.

To this end, in particular for a laser operating at 224 nm, a so-called substractive monochromator may be used which is placed between the elliptical cell and the Raman scattering study spectrograph. This subtractive monochromator eliminates a spectral band of luminous energy. To eliminate the luminous energy relating to the Laser emission wavelength, the subtractive monochromator is locked onto the laser emission wavelength, combined with a bandwidth defined in such a way that all the luminous energy from the Laser is indeed eliminated.

The study spectrograph for the Raman emission has moreover a specific constraint: the more effective it is (more exactly, the greater is the fineness of the spectrum analysis it can perform), the finer must be the cone of light it can analyse on its input. A cone of light of the order of a few degrees is required to obtain acceptable performance.

Because of the reflections specific to the operation of the elliptical cell, the beam of light collected at the second focal point takes the shape of a divergent cone at the cell output. Its angle of opening at the apex depends on the geometry of the elliptical cell. This angle may typically be between 30 and 90°. Such an opening is not compatible with the admission conditions for a beam to be analysed at the spectrograph input.

Of course a lens could be used to correct this divergence, placed in such a way that its focal point coincides with the ellipse's second focal point. However, as was explained above, such a lens has the disadvantage of having behaviour which depends on the wavelength used.

According to an embodiment for the invention, the use of an elliptical mirror light concentrator is proposed to concentrate a beam of divergent light. The concentrator's first focal point is placed on the second elliptical cell focal point, and its second focal point is located at the monochromator's input slot. This arrangement may provide the means for example of dividing the opening angle for the cone of light coming from the elliptical cell by a factor of 10.

In such a device adapted specifically to odour detection, a gas flow licks the biological receptor consisting of an olfactory receptor fixed at the end of the support That olfactory receptor thus continually emits a Raman spectrum. This Raman spectrum is collected by the elliptical cell, concentrated by the elliptical mirror concentrator, filtered and cleared of reflections from the excitation laser by a filter or a subtractive monochromator and is analysed by the spectrograph which gives the Raman spectrum for the olfactory receptor. When the olfactory receptor binds an odour molecule borne by the flow, the Raman spectrum produced undergoes changes relative to that for the olfactory receptor alone. The Spectrograph is thus able to detect those changes and subsequently indicate the presence or the absence of an odorous molecule on the olfactory receptor.

According to an embodiment variant, more than one olfactory receptor can be installed at the end of the silica longitudinal support. The longitudinal support may be inserted inside a silica tube which is transparent to UV.

The Raman effect of each of the olfactory receptors is measured sequentially so that each olfactory receptor is lit in turn by the laser beam. This function may be provided either by moving the longitudinal support or by moving the elliptical cell. The mechanical movements of the longitudinal support or the elliptical cell may be achieved in step by step mode or continuously. Suitable software means allow for controlling the spectrograph and thus isolating the various Raman spectra relating to the olfactory receptors placed on the support. This variant provides the means for much more complete analyses of the odour molecules contained in the fluid.

The tube in which the gas flow to be analysed circulates is dimensioned according to the specifications required, namely it either conveys the gas flow directly onto the olfactory receptors or it contains itself the support for all of the olfactory receptors.

BRIEF DESCRIPTION OF THE DRAWINGS

The invention will be understood better and other advantages and specific features will appear on reading the description which follows which is given as a non-limiting example, accompanied by the annexed drawings, wherein.

DETAILED DESCRIPTION OF PREFERRED EMBODIMENTS

Figure 1A:
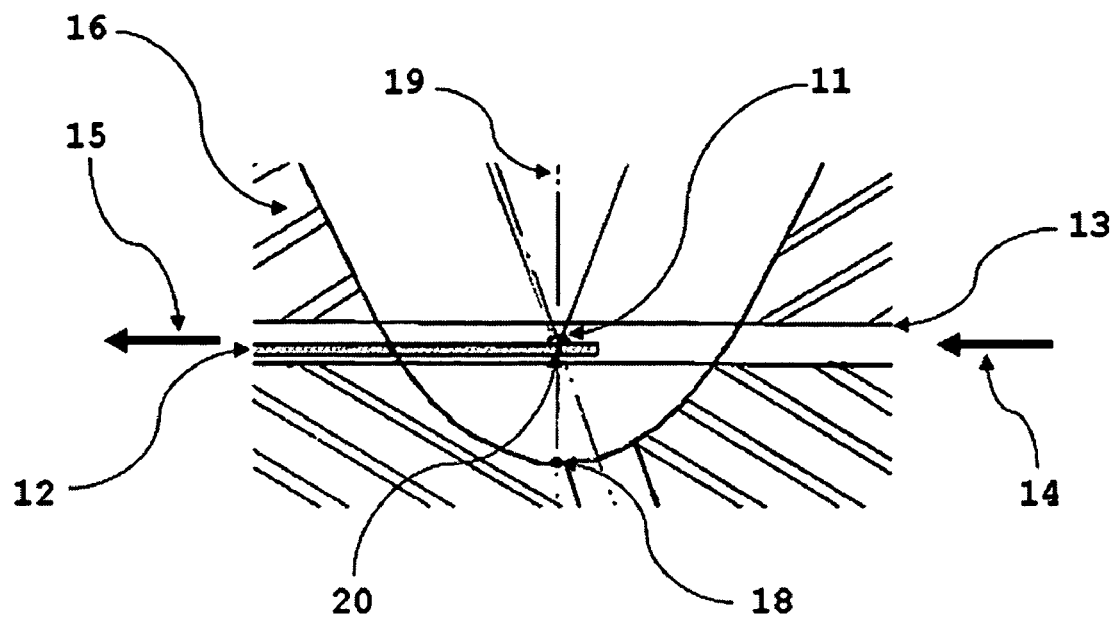
FIGS. 1a and 1b are cross-sectional views illustrating schematically, in FIG. 1a, a situation where the gas flow together with the support for the olfactory receptors are contained in a tube, and, in FIG. 1b, a situation where the gas flow is conveyed by a tube on the support for the olfactory receptors.

FIG. 1a is a detailed longitudinal cross-sectional view illustrating schematically the position of a tube containing an olfactory receptor in the device for this example.

An olfactory receptor 11 is positioned on a longitudinal support 12 made of silica which is transparent to UV and the support/olfactory receptor assembly is inserted in a tube 13 which is transparent to UV wavelengths (between 200 nm and 300 nm in particular) in such a way that a liquid or gas fluid can circulate between an input and an output indicated by arrows 14 to 15. The tube is inserted into an aluminium cell 16 which has a concave reflective surface 17 in ellipsoid form with an axis of revolution 19 for which one of the crowns is indicated at 18. In this, the tube crosses the elliptical cell perpendicularly to the axis 19 is such a way that the olfactory receptor is positioned at a focal point 20 relating to the crown 18 for the elliptical cell.

Figure 1B:
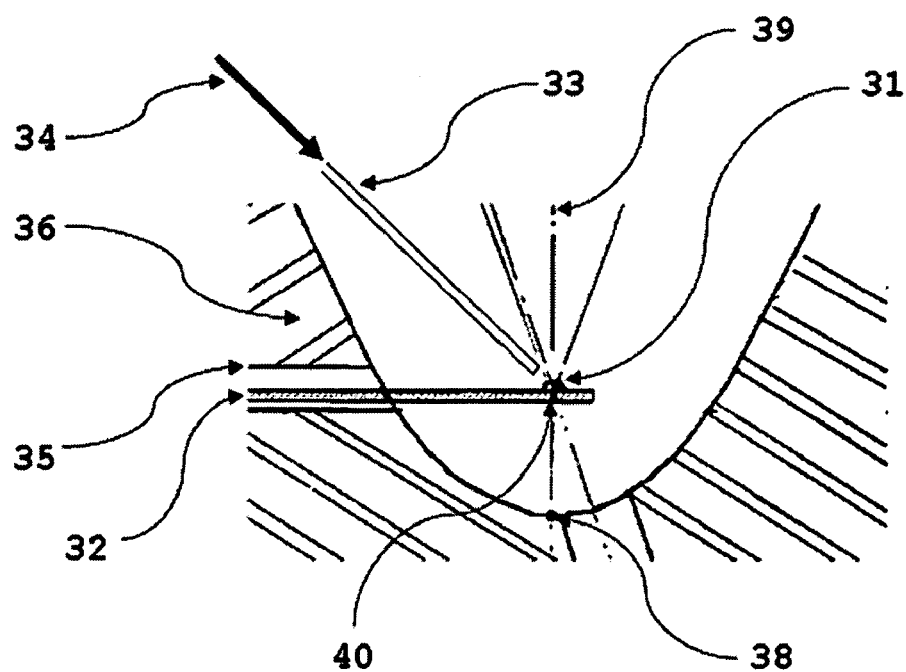

FIG. 1b is a detailed longitudinal cross-sectional view illustrating schematically the position of an olfactory receptor 31 in the device and the position of a tube 33 which conveys a gas flow in a cell 36.

The olfactory receptor 31 is positioned on a longitudinal support 32, here perpendicular to the axis 39, and the support/olfactory receptor assembly is inserted into a drilling 35 in the elliptical cell 36 in such a way that the olfactory receptor 31 is positioned at a focal point 40 of the elliptical cell. The tube 33 conveys the gas flow onto the olfactory receptor in an oblique direction 34 relative to the axis 39 for the cell 36.

Figure 2:
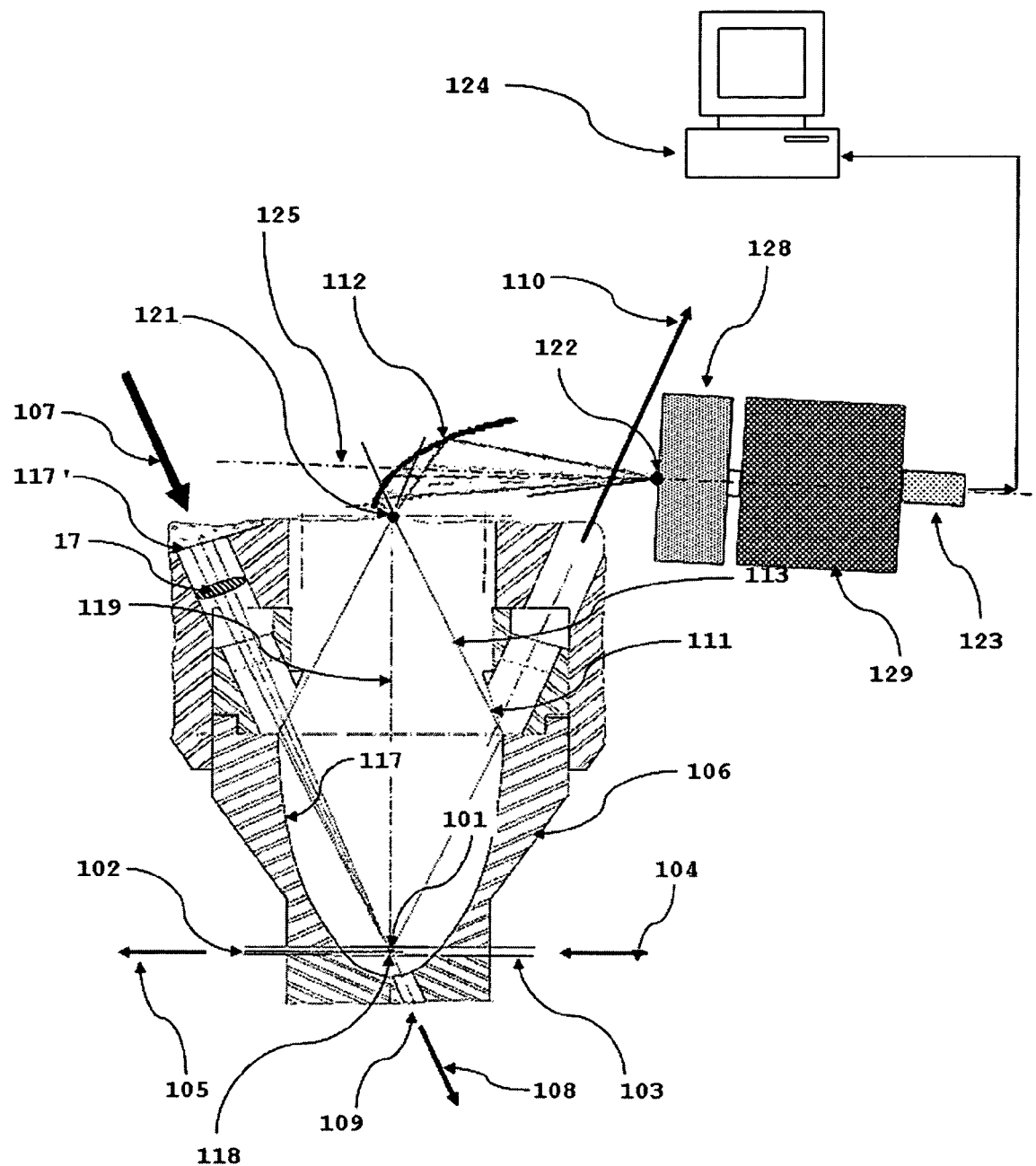
FIG. 2 is a cross-sectional view illustrating schematically a Raman effect collection process according to the invention.

FIG. 2 is a detailed view of a device for collecting the olfactory receptor's Raman effect.

A tube 103, containing a support 102 for an olfactory receptor 101, as in FIG. 1a, is positioned inside an elliptical cell 106 in such a way that the olfactory receptor is placed at the elliptical cell's focal point 118 and receives the samples of gas to be analysed, conveyed by the tube in the direction illustrated by the arrows 104 and 105.

A laser beam 107 is brought inside the cell by a canal 117' at an oblique direction relative to the axis 119 for cell 106. It is focussed through a lens 17 in that canal onto the olfactory receptor 101 after crossing the tube 103. A part 108 of the laser beam then crosses the support 102, then the opposite wall of the tube 103, and is let out by an orifice 109 so as to prevent direct reflections on the elliptical cell's wall. Another part 110 of the laser beam is reflected by the support 102 and is let out by an orifice 111 and a symmetrical canal of the canal 117' through the cell body, again so as to prevent parasite reflections of the laser beam on the elliptical cell's reflecting wall 117.

An elliptical mirror 112 (or beam concentrator) has the form of a half shell semi-ellipsoidal on one side of a plane passing by the major axis of the half ellipsoid and open in the direction of the cavity in cell 106 on the other side. It is positioned at the output of the elliptical cell 106 in such a way that its first focal point 121 coincides with the second focal point of the elliptical cell (opposite the focal point 118 where the receptor 101 is located) and so that its second focal point 122 coincides with the input for an optical component 128. The mirror 112 is directed in such a way that it reflects all the luminous rays 113 coming from the receptor 101 and reflected by the elliptical cell. Its optical axis 125 (not to be confused with the major axis 127 of the half ellipsoid 112) is defined as the axis which represents the maximum luminous energy collected at the focal point 122. This axis does not correspond to the beam's geometric axis, insofar as the measurement or collection of the luminous signals 113 by the elliptical mirror 112 is not linear.

A first optical component 128 is positioned around the optical axis 125 of the optical reflector 112. The purpose of this optical component is to eliminate the reflections coming from the excitation luminous energy 107. The optical component may be a rejection optical filter (which may also be called Notch), insofar as it is available for the wavelength of the excitation beam luminous energy 107 (wavelength in the visible range), or a subtractive-type monochromator for wavelengths in the UV (between 200 and 300 nm) and in particular for the 224 nm wavelength.

A spectrograph 129 is placed at the outlet of the monochromator 128 illustrated here to provide the detection of the Raman spectrum. It is aligned on the optical axis 125.

The luminous energy coming from the spectrograph is collected by an optical component 123 of the photo-multiplier tube type or CCD camera or photon counter.

The Raman spectra are processed, stored and compared by a data processing system 124. It provides the means for identifying the Raman scattering spectrum rays obtained and comparing them with the reference records in its database. The comparison gives information on any binding of an odorous molecule on the olfactory receptor 101.

Figure 3:
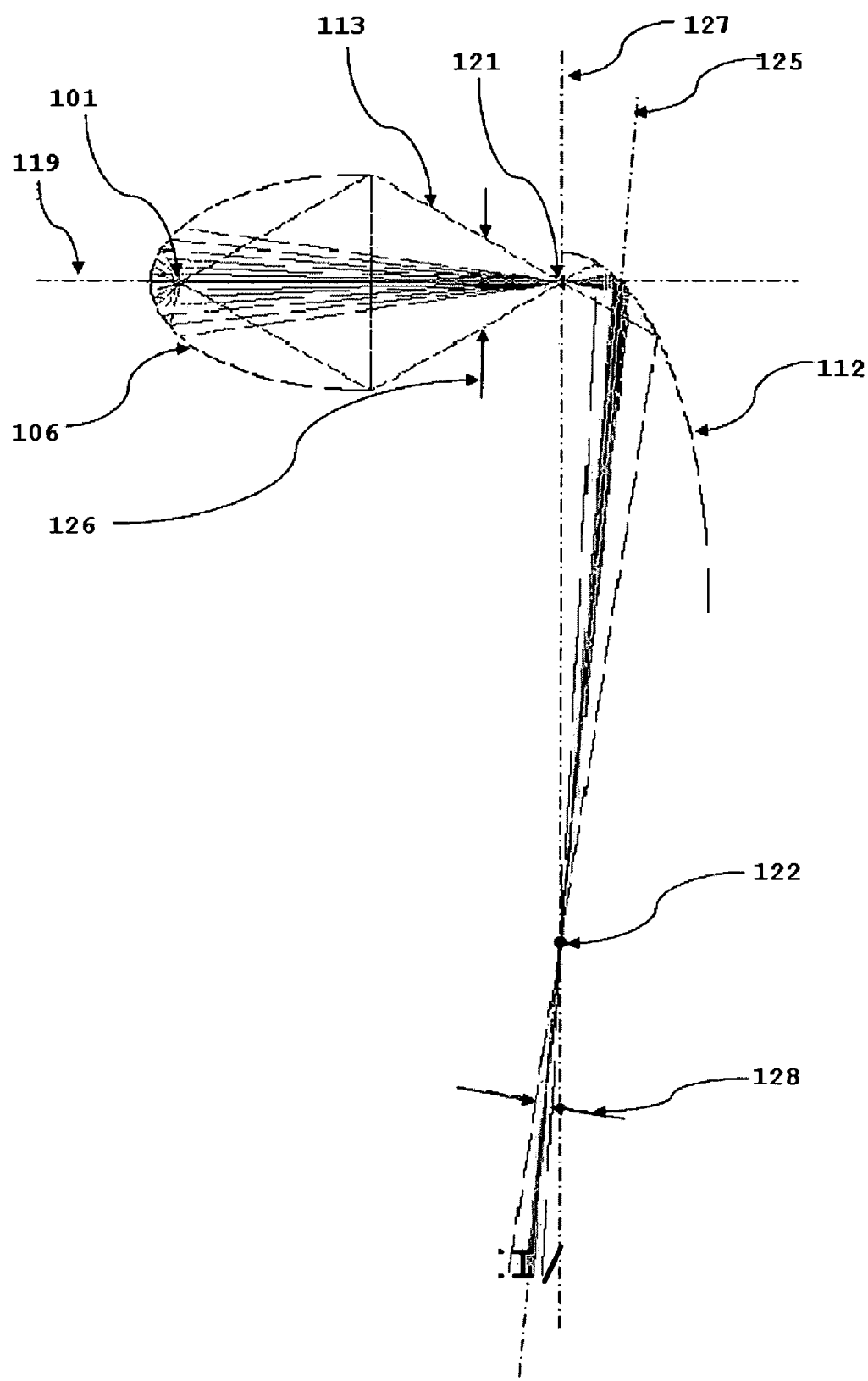
FIG. 3 is an optical diagram representing the operation of the elliptical mirror light concentrator, FIG. 4, consisting of FIGS. 4a and 4b, illustrates a matrix of sensors in FIG. 4a and three positions of that matrix relative to the point of impact of the incident laser beam in FIG. 4b.

FIG. 3 shows the operation of the elliptical mirror 112 (or light concentrator) combined with the elliptical cell 106. The olfactory receptor 101 is placed at the first focal point of the elliptical cell 106. The light beam 113 collected by the cell 106 is contained in a cone defined by the angle at the apex 126. This angle is between 0 and 180°, but typically between 30 and 160°. In the embodiment example in FIG. 3, the angle is 60°. The elliptical mirror (or light concentrator) 112 is positioned on the elliptical cell 106 in such a way that one of its focal points 121 coincides with the second focal point of the ellipse and so that, in this specific embodiment, its axis 127 is perpendicular to the revolution axis 119 of the elliptical cell 106. The elliptical mirror reflects the light, concentrating it into an angled conical beam at the apex 128 and focuses it at the second focal point 122 of the elliptical mirror. The angle at the apex of the light cone at the focal point 122 is reduced relative to the angle 126 by a factor which is linked to the parameters of the elliptical mirror 112 and may attain 10 (ten) or more. In the representation in FIG. 3, the angle 128 is 5.75°.

The optical axis 125 is defined as the axis on which the power collected by the mirror 112 is at a maximum.

Figure 4A:
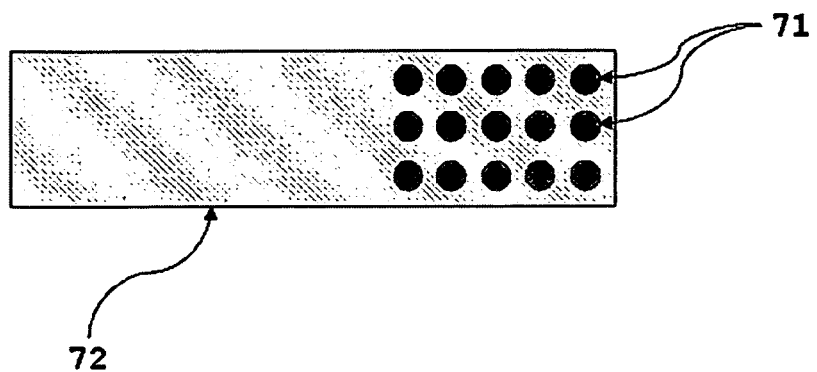

FIG. 4a is a detailed top view of the longitudinal support, with several olfactory receptors.

Olfactory receptors 71 are positioned on a longitudinal support 72. The number of them, fifteen here in three rows of five receptors, is not restrictive and depends on the performance required in terms of odour detection.

Figure 4B:
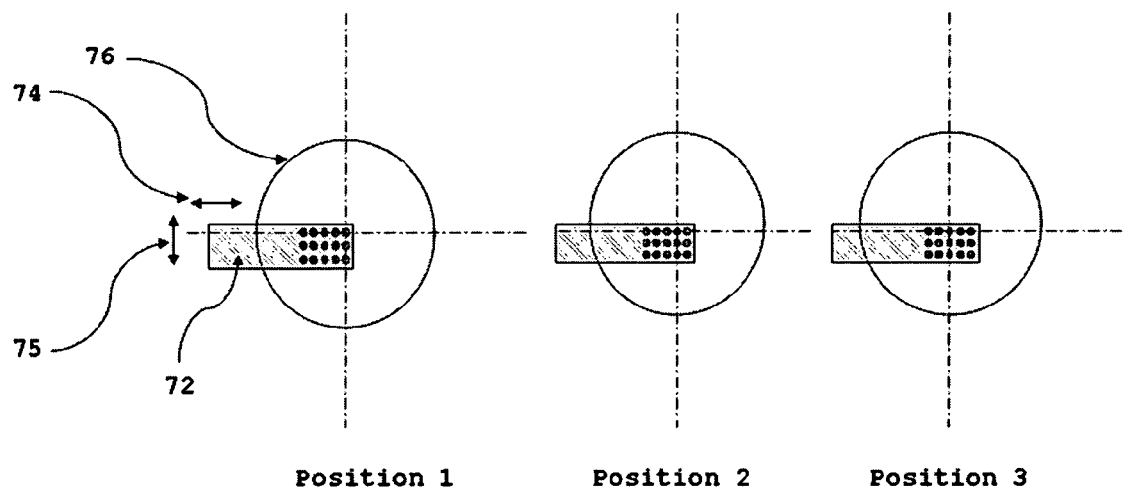

FIG. 4b is a top view, the cross-section being made at the elliptical cells focal point represented diagrammatically 76, and in a plane perpendicular to the revolution axis for the elliptical cell 76. It shows the movements in both orthogonal directions 74 and 75 of the longitudinal support 72 relative to the elliptical cell. In this way each olfactory receptor 71 can be presented in turn to the elliptical cell's focal point 80. Thus the Spectrograph is able to collect the Raman spectrum relating to each of those receptors. Either elliptical cell 76 is fixed and it is the longitudinal support 72 which moves or the longitudinal support is fixed and it is the elliptical cell which moves.

FIG. 4b shows an example where the support holds 15 olfactory receptors. There will thus be 15 different positions for the support or the cell. FIG. 4b illustrates 3 positions for the interrogation of 3 cells in the upper row in the figure.

Of course, the principles described above may be extended to other types of measurements and mediums whether they are liquid or gas and also to continuous or discontinuous measurements.

The invention claimed is:

1. A method for analysing a medium in searching for an odorous biological molecule characteristic of a specific substance in an environment to be studied, comprising the following steps:
    exposing a component containing at least one olfactory biological receptor capable of selectively attaching the type of odorous molecule sought to an atmosphere sampled from the environment to be studied,
    irradiating the component with an incident laser radiation the wavelength of which is chosen in the ultraviolet close to the olfactory receptor's absorption wavelength to cause the excitation of resonance Raman scattering in the component irradiated and
    analysing the Raman spectrum obtained to determine whether or not it corresponds to the Raman spectrum of the olfactory receptor having attached an odorous molecule of the type sought in the atmosphere sampled so as to identify the possible presence of the said substance in the environment to be studied.

2. A method according to claim 1, wherein the incident laser radiation wavelength is selected in the 200 nm to 300 nm range.

3. A method according to claim 1, wherein the incident laser radiation wavelength is selected in the 200 nm to 250 nm range.

4. A method according to claim 1, wherein the incident laser radiation wavelength is 224 nanometers.

5. A method according to claim 1, wherein the component is excited by the laser radiation at a quasi-punctual zone and the light emitted by the component in response is captured in a solid angle greater than 10% in the space surrounding that quasi-punctual zone.

6. A method according to claim 5, wherein the light emitted by the component in response is captured by a reflective surface of a concave elliptical profile in an analysis cell, a first focal point of which has been positioned in that quasi-punctual zone, and the reflected radiation is collected in a second quasi-punctual zone in the second focal point of the reflective elliptical surface.

7. A method according to claim 6, wherein the energy relating to the incident laser beam's wavelength is eliminated from the reflected radiation.

8. A method according to claim 1, wherein fluid liable to contain odorous molecules coming from the environment studied is circulated to bring it into contact with the component containing the olfactory receptor (OR).

9. A method according to claim 8, wherein that fluid is circulated in contact with a battery of sensors each having one specific OR and the sensor or sensors relating to that or to those of the olfactory receptors (OR) which attached an odorous molecule are detected to obtain information relevant for identifying the specific substance at the origin of the odour.

10. A method for detecting the association of a biological receptor with its or one of its specific ligands, after that biological receptor has been exposed to a medium liable to contain that ligand, comprising the following steps: irradiating said biological receptor with an incident laser radiation the wavelength of which is chosen in the ultraviolet close to the biological receptor's absorption wavelength to produce resonance Raman scattering in said irradiated receptor, and analysing the Raman spectrum obtained to determine whether or not it corresponds to a resonance Raman scattering spectrum already identified for the receptor combined with its or one of its specific ligands.

11. A method for detecting the association of a biological receptor with its or one of its specific ligands, after said biological receptor has been exposed to a medium liable to contain that ligand, comprising the following steps: irradiating a quasi-punctual zone of that biological receptor with an incident radiation laser whose wavelength is chosen in the ultraviolet close to the absorption wavelength for the biological receptor in question to produce resonance Raman scattering in said irradiated receptor, collecting light emitted in response by the component, in a solid angle greater than 10% in the space surrounding said quasi-selective zone, detecting the resonance Raman scattering spectrum contained in the light collected and analysing such spectrum to determine whether or not it has the characteristics of resonance Raman scattering spectrum already identified for said biological receptor combined with its or one of its specific ligands.

12. A method according to claim 11, wherein, to collect the light emitted in response, said light is captured on a reflective surface substantially of concave ellipsoidal revolution profile in a cell, for which a first focal length has been positioned in that quasi-selective zone, and the reflected radiation is collected in a second quasi-punctual zone at the second focal point of the reflective elliptical surface before dispersing its spectrum.

13. Apparatus for detecting the presence of certain substances capable of producing odorous molecules in an environment to be studied, comprising:
    an analysis cell to accommodate at least one olfactory biological receptor in a quasi-punctual zone thereof,
    a device for presenting a sample taken from the atmosphere of the environment to be studied to said receptor in the cell,
    a UV laser source to irradiate said receptor in the cell with an incident beam of coherent light having a wavelength in the ultraviolet sufficiently close to the absorption wavelength of the olfactory receptor in question so as to excite resonance Raman scattering in that receptor, the cell further including means for collecting the light emitted by the olfactory receptor in response to the irradiation by said incident beam in a solid angle greater than 10% of the space surrounding the quasi-punctual zone to concentrate it in a second quasi-punctual zone which is spatially separate from the receptor and located away from the axis of the incident laser beam, a spectrum analysis device for analysing radiation light concentrated in the second quasi-punctual zone at wavelengths close to that of the incident beam to detect the resonance Raman scattering spectrum and means for processing the Raman spectrum obtained, which can hold reference data relating to the Raman scattering spectra for that olfactory biological receptor when it is combined with an odorous molecule of the type sought, to determine whether the sample taken contains such an odorous molecule indicative of a specific substance in the environment to be studied.

14. Detection apparatus according to claim 13, wherein the laser's wavelength is between 200 and 250 nanometers.

15. Detection apparatus according to claim 13, further comprising an elliptical concentrator mirror having an input focal point placed in that quasi-punctual zone to convert the light energy concentrated in that quasi-punctual zone into a light pencil beam capable of being admitted to the input of said spectrum analysis device.

16. Detection apparatus according to claim 13, further comprising means for eliminating from the light concentrated in the second quasi-punctual zone light rays whose wavelength is the same as that for the incident laser beam.

17. Detection apparatus according to claim 16, wherein said eliminating means include a substractive-type monochromator having an input slot positioned to receive a significant part of the radiation concentrated in the second quasi-punctual zone.

18. Detection apparatus according to claim 16, wherein said eliminating means include an optical filter at the concentrator output.

19. Detection apparatus according to claim 13, wherein the means for collecting the light produced in response to the excitation of the olfactory receptor comprise a specific concave reflective surface in that cell to reflect the radiation coming from the receptor in said solid angle in order to concentrate the emergent light to that second quasi-punctual zone.

20. Detection apparatus according to claim 19, wherein the reflective surface has a substantially ellipsoidal profile with its two focal points each located respectively in one of those quasi-punctual zones.

21. Detection apparatus according to claim 13, wherein the sample presentation device comprises a device for circulating the fluid taken from the environment to be analysed close to said first quasi-punctual zone in the analysis cell.

22. Detection apparatus according to claim 13, wherein the analysis cell has a support for holding a plurality of separate olfactory receptors and means specific for moving the support relative to the irradiation first punctual zone.

23. Detection apparatus according to claim 13, wherein the laser's wavelength is 224 nanometers.

* * * * *